(12) United States Patent
Beier et al.

(10) Patent No.: US 7,220,473 B2
(45) Date of Patent: May 22, 2007

(54) ABSORBING AGENTS AND COVER LAYER WHICH IS IMPERMEABLE TO ACTIVE SUBSTANCES AND WHICH CONTAINS CHANNEL-FORMERS OR REMOVABLE PROTECTIVE LAYER OF A TRANSDERMAL THERAPEUTIC SYSTEM

(75) Inventors: Cornelia Beier, Holzkirchen (DE); Ralf Kibele, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 164 days.

(21) Appl. No.: 10/433,373

(22) PCT Filed: Dec. 5, 2001

(86) PCT No.: PCT/EP01/14280

§ 371 (c)(1), (2), (4) Date: Sep. 11, 2003

(87) PCT Pub. No.: WO02/45700

PCT Pub. Date: Jun. 13, 2002

(65) Prior Publication Data
US 2004/0047901 A1 Mar. 11, 2004

(30) Foreign Application Priority Data
Dec. 6, 2000 (DE) .............................. 100 60 852

(51) Int. Cl.
- *A61L 2/00* (2006.01)
- *B32B 33/00* (2006.01)
- *B32B 37/00* (2006.01)

(52) U.S. Cl. .................... 428/40.2; 427/2.1; 428/40.1; 428/40.4; 428/40.9; 428/41.3; 428/41.7; 428/42.1; 428/323; 428/325; 428/327; 524/492; 524/493; 602/57; 602/58; 602/900

(58) Field of Classification Search ............... 428/40.1, 428/40.2, 40.4, 40.9, 41.3, 41.7, 42.1, 323, 428/325, 327; 427/2.1; 524/492, 493; 602/57, 602/58, 900
See application file for complete search history.

(56) References Cited

U.S. PATENT DOCUMENTS 5,911,937 A 6/1999 Hekal .................. 264/255

(Continued)

FOREIGN PATENT DOCUMENTS

EP 0 399 765 11/1990

(Continued)

OTHER PUBLICATIONS

D. Satas, Handbook of Pressure Sensitive Adhesive Technology, "Acrylic Adhesives", 2nd Ed., pp. 396-456, Van Nostrand Reinhold, NY (1989).

(Continued)

Primary Examiner—Nasser Ahmad
(74) Attorney, Agent, or Firm—Licata & Tyrrell P.C.

(57) ABSTRACT

This present invention concerns a cover layer that is impermeable to the active substances and/or a removable protective layer of a transdermal therapeutic system, comprising a thermoplastic film which either directly contains the absorbing agents and channel-forming agents or is coated with a polymer support (thermoplast) containing these substances. The polymer support can either be applied over the entire surface of the film or in patterns, directly during production. The thermoplastic film that is used and the polymer support can be made from either the same or different materials.

8 Claims, 11 Drawing Sheets

U.S. PATENT DOCUMENTS

2004/0247656 A1* 12/2004 Beier et al. .......... 424/449
2004/0253299 A1* 12/2004 Beier et al. .......... 424/449

FOREIGN PATENT DOCUMENTS

| WO | WO 97/32663 A | 9/1997 |
| --- | --- | --- |
| WO | WO 98/39231 A | 9/1998 |
| WO | WO 99/61855 A | 12/1999 |
| WO | WO 99/61856 | 12/1999 |
| WO | WO 99/62697 | 12/1999 |
| WO | WO 99/63288 | 12/1999 |
| WO | WO 00/16884 | 3/2000 |
| WO | WO 00/17258 | 3/2000 |
| WO | WO 00/17259 | 3/2000 |
| WO | WO 00/17260 | 3/2000 |

OTHER PUBLICATIONS

Loretta A. Sobieski, et al., "Silicone Pressure Sensitive Adhesives", D. Satas, Handbook of Pressure Sensitive Adhesive Technology, 2nd Ed., pp. 508-517, Van Nostrand Reinhold, NY (1989).

* cited by examiner

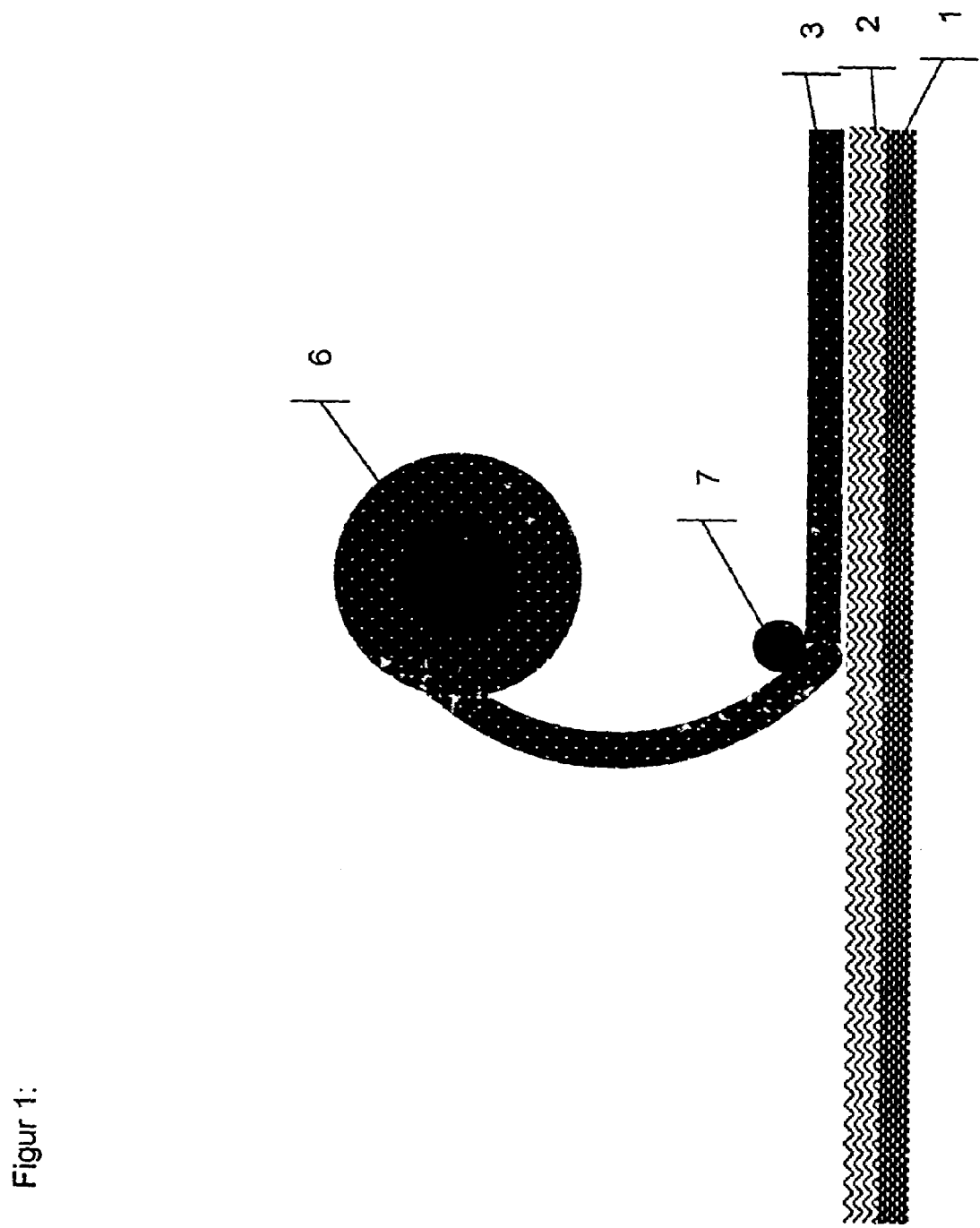
Figur 1:

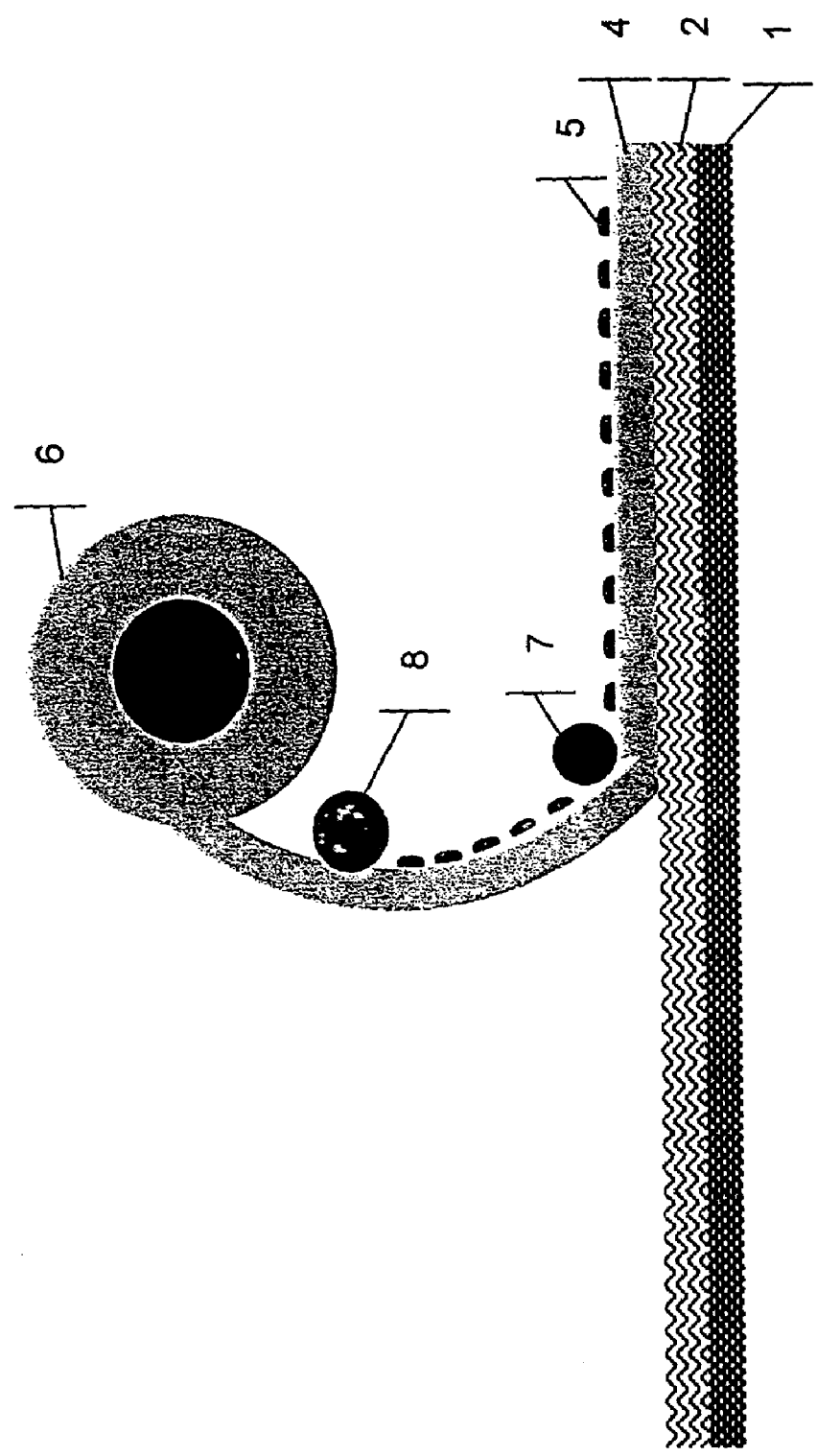
Figur 2:

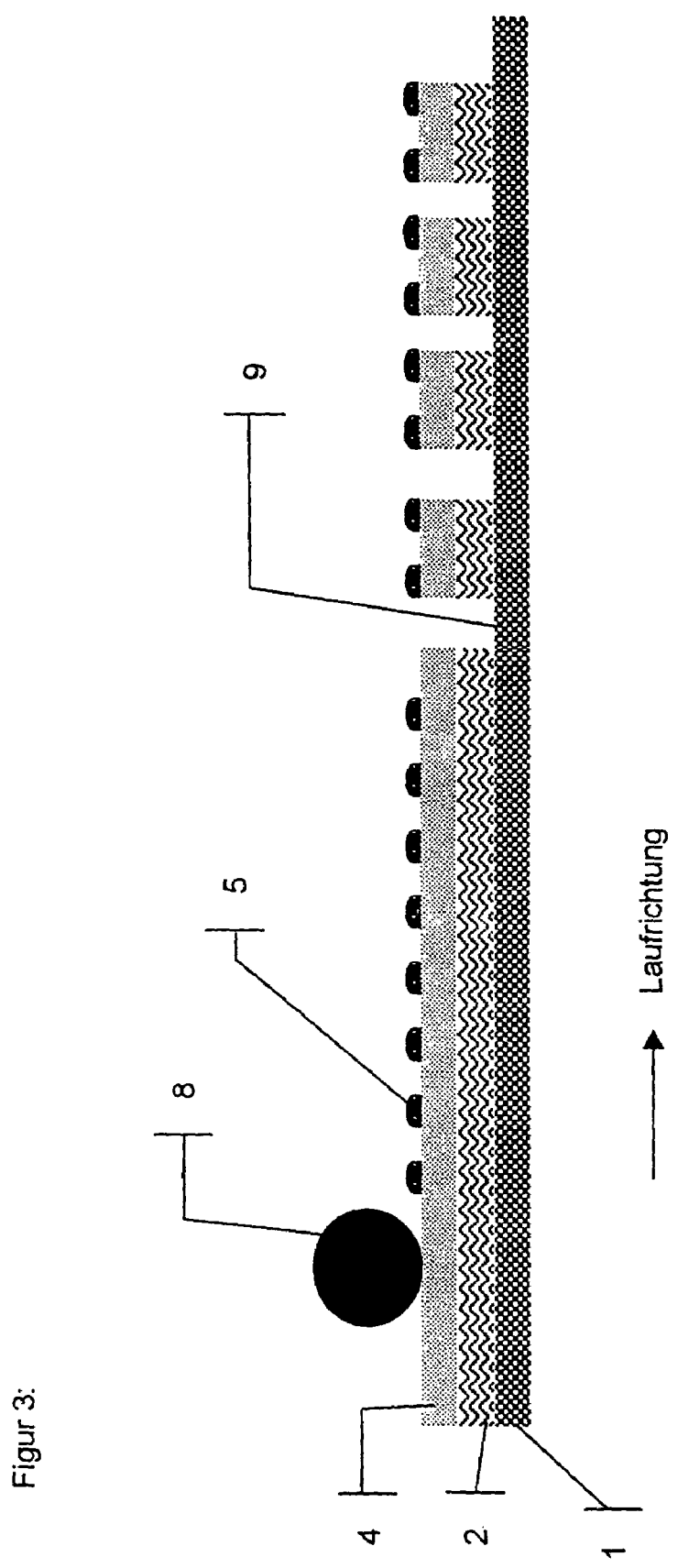

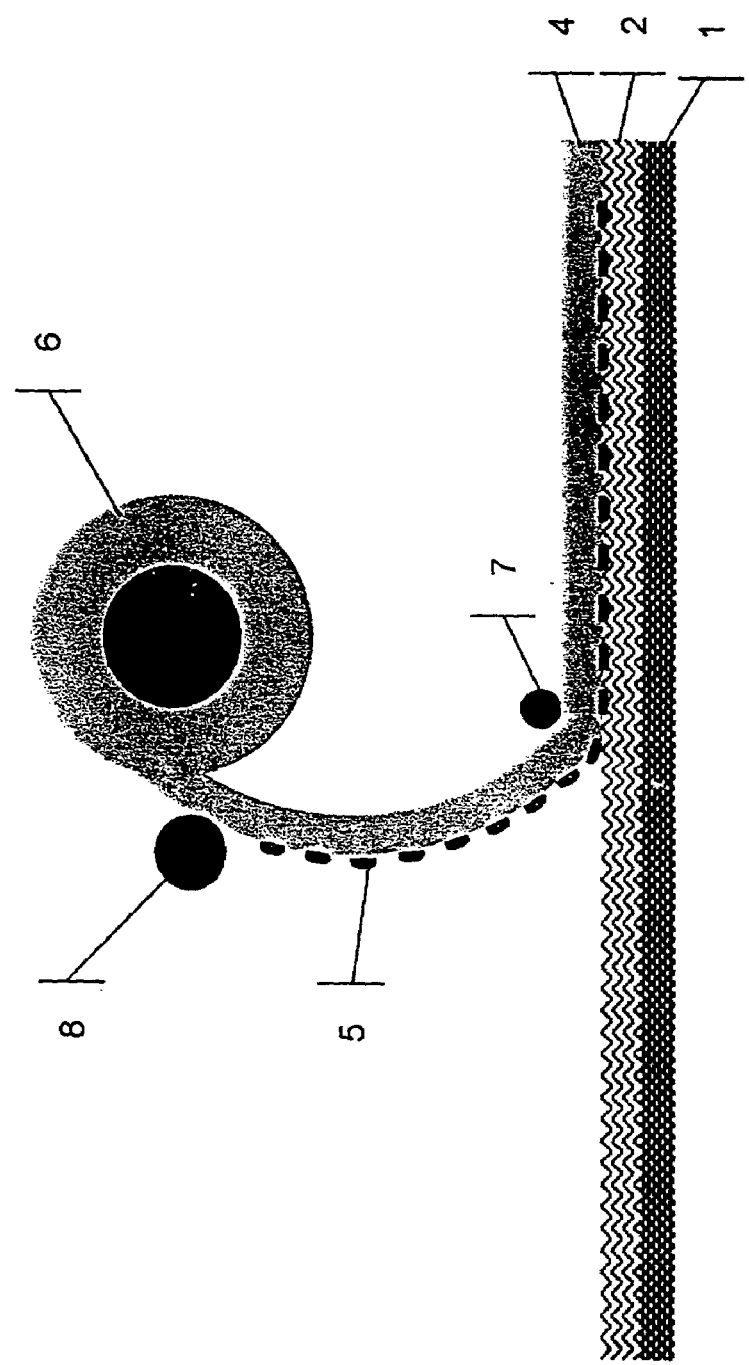
Figur 4:

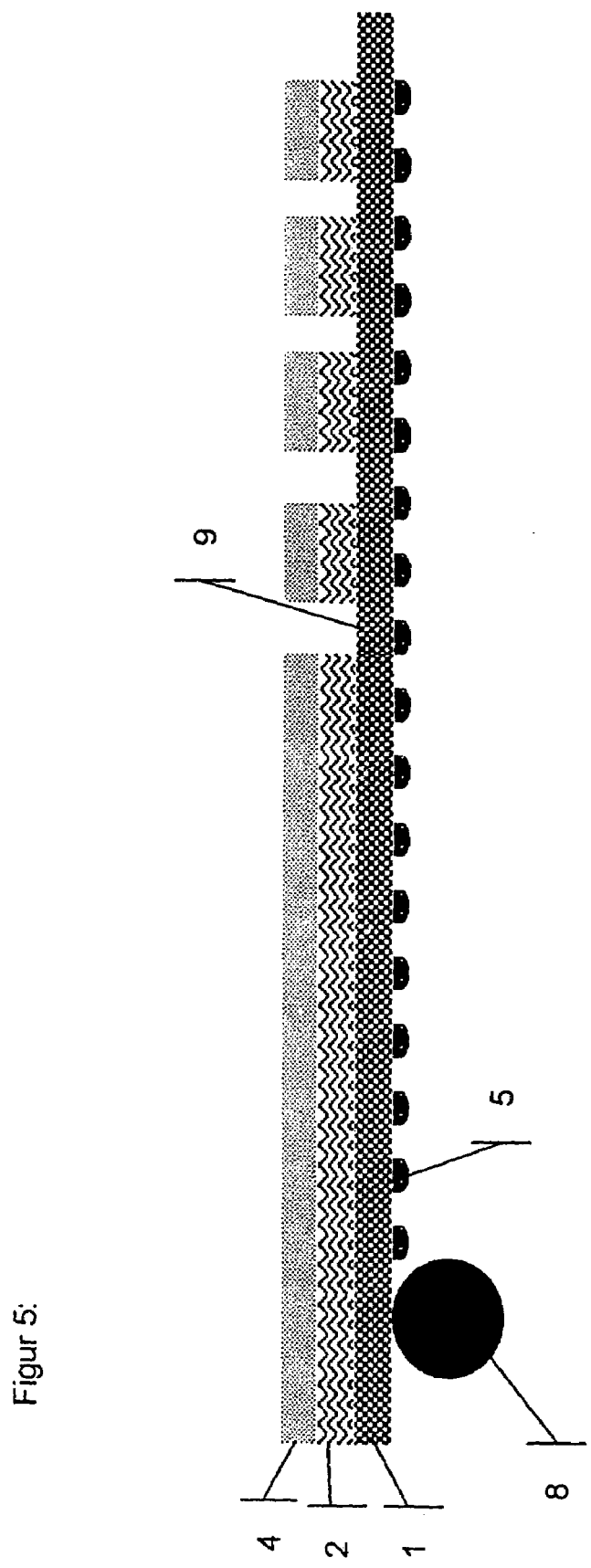
Figur 5:

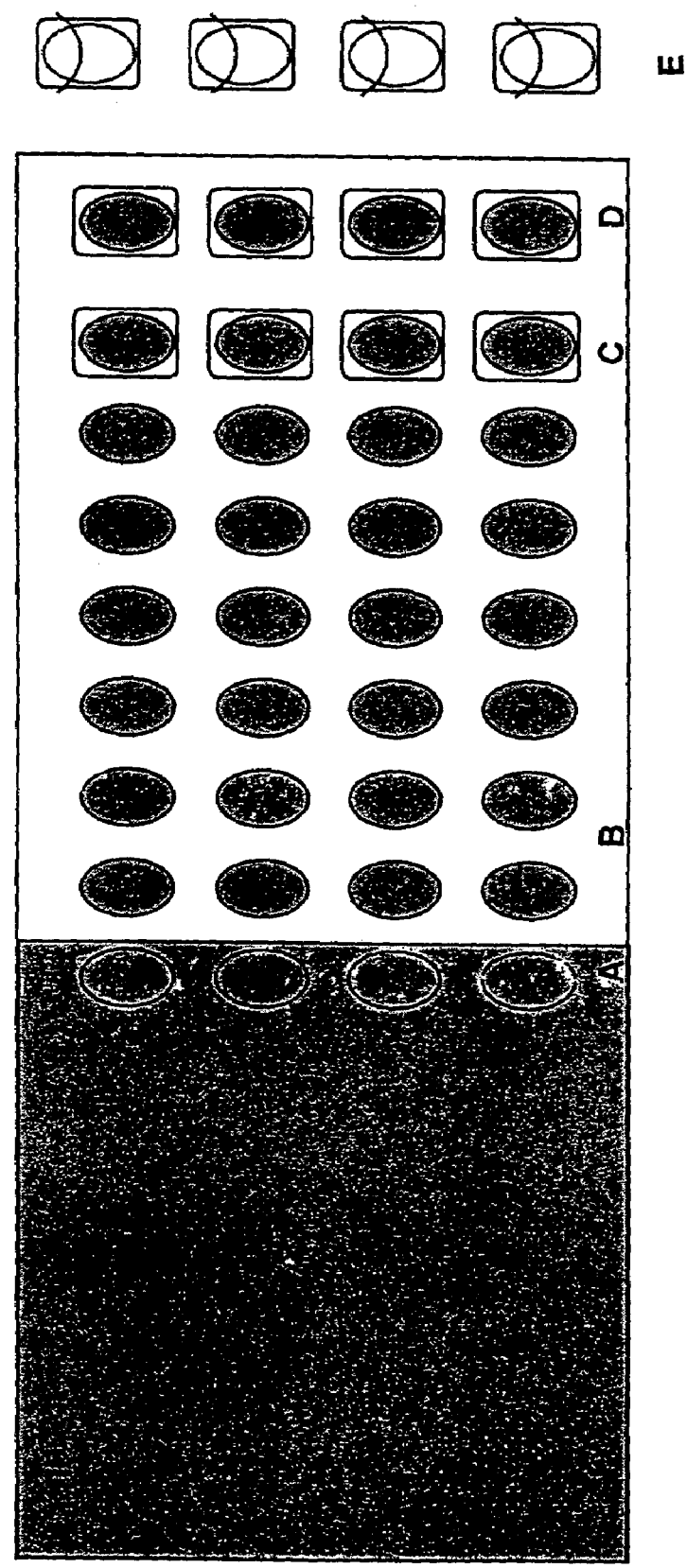
Figur 6:

Figur 7:
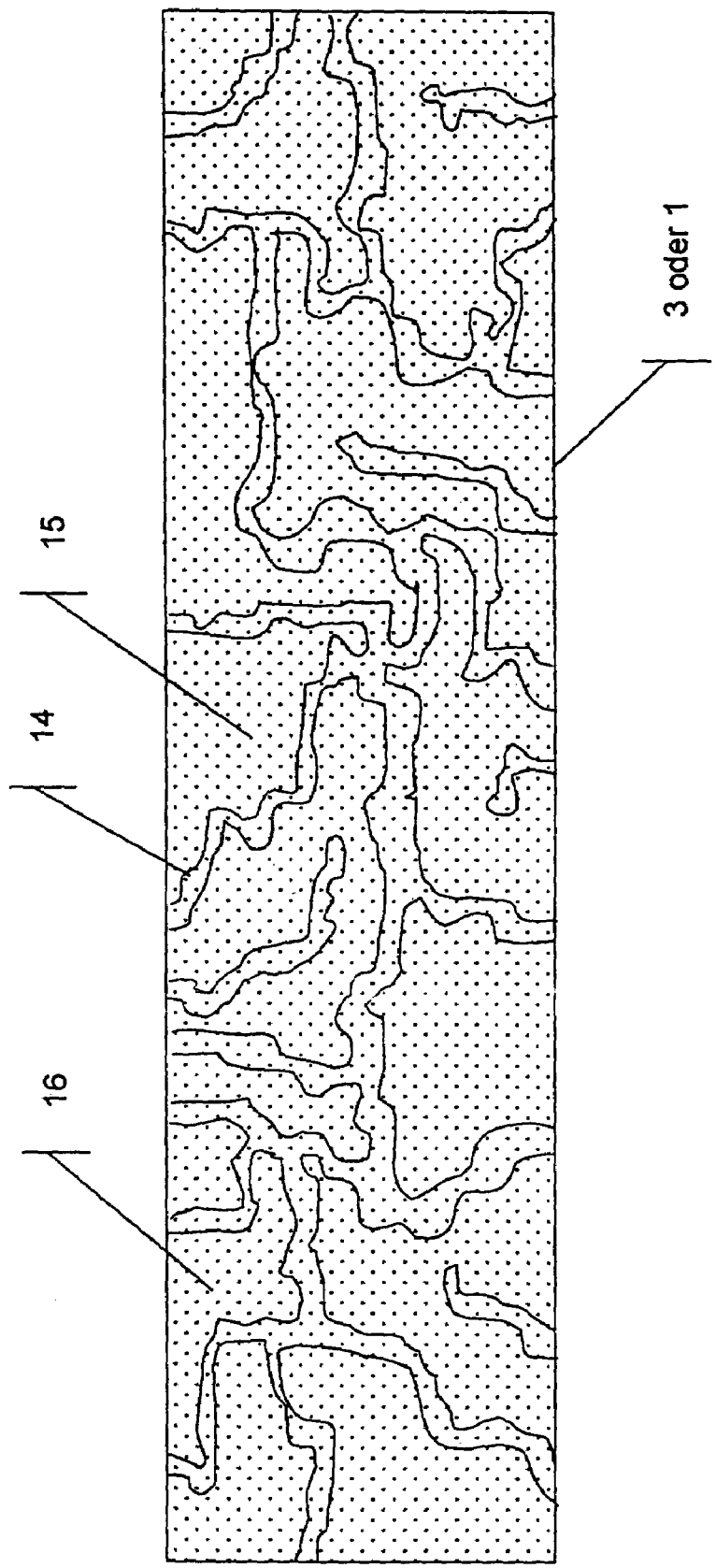

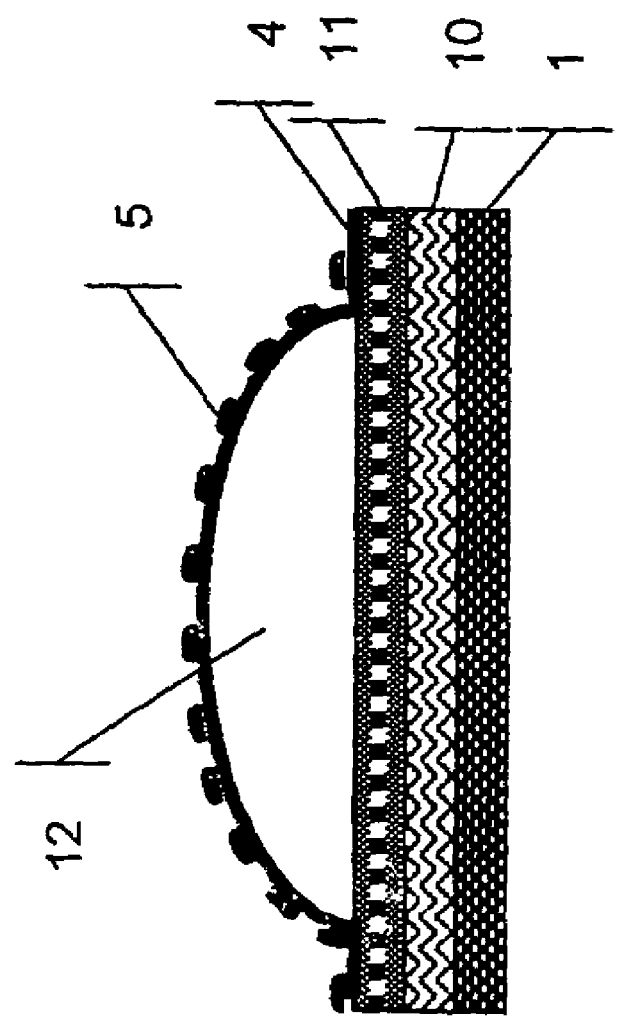
Figur 8:

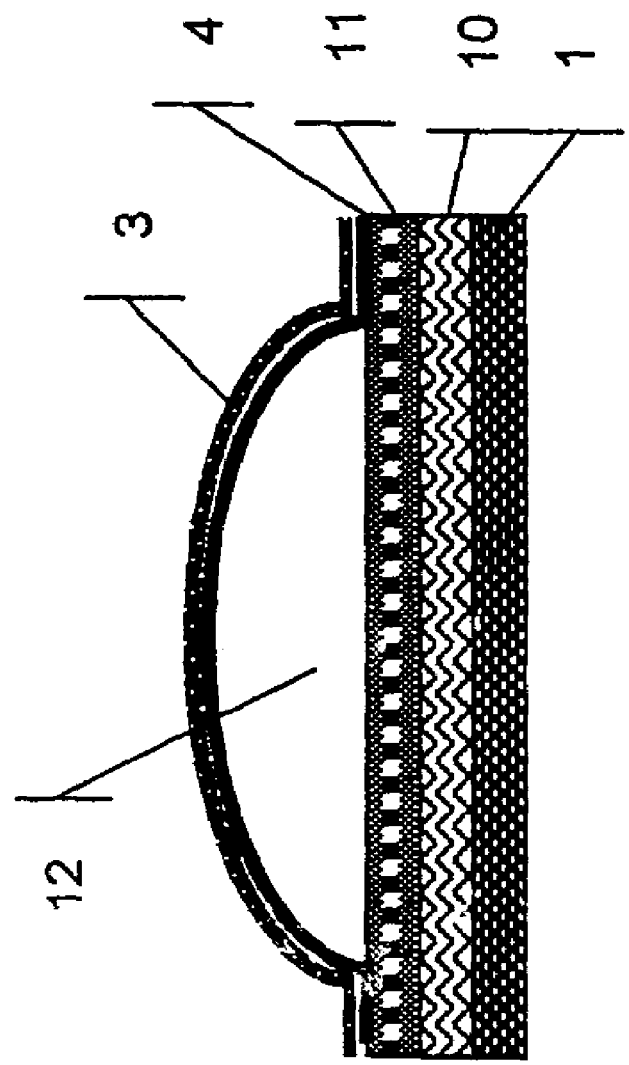
Figur 9:

Figur 10:
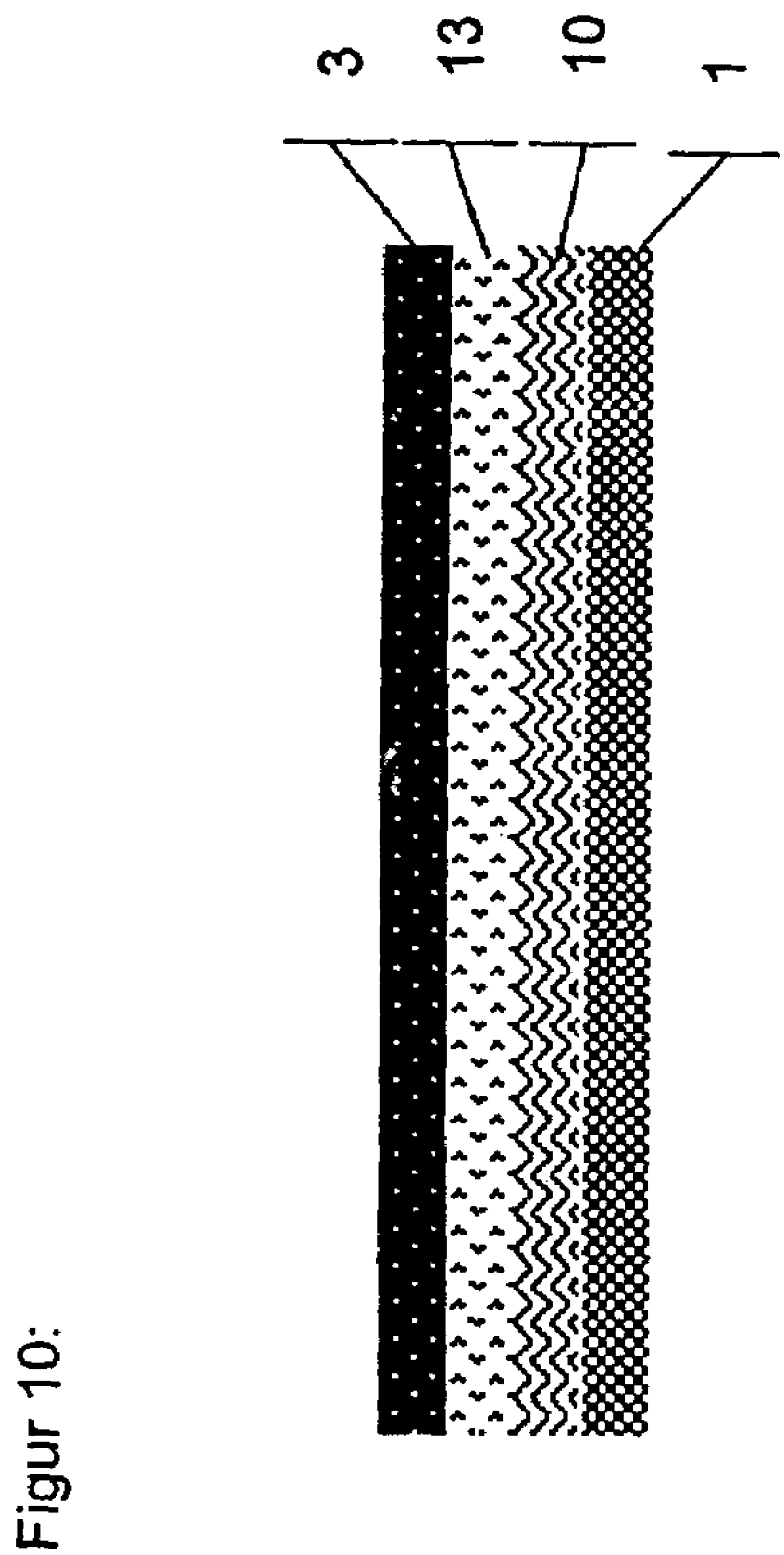

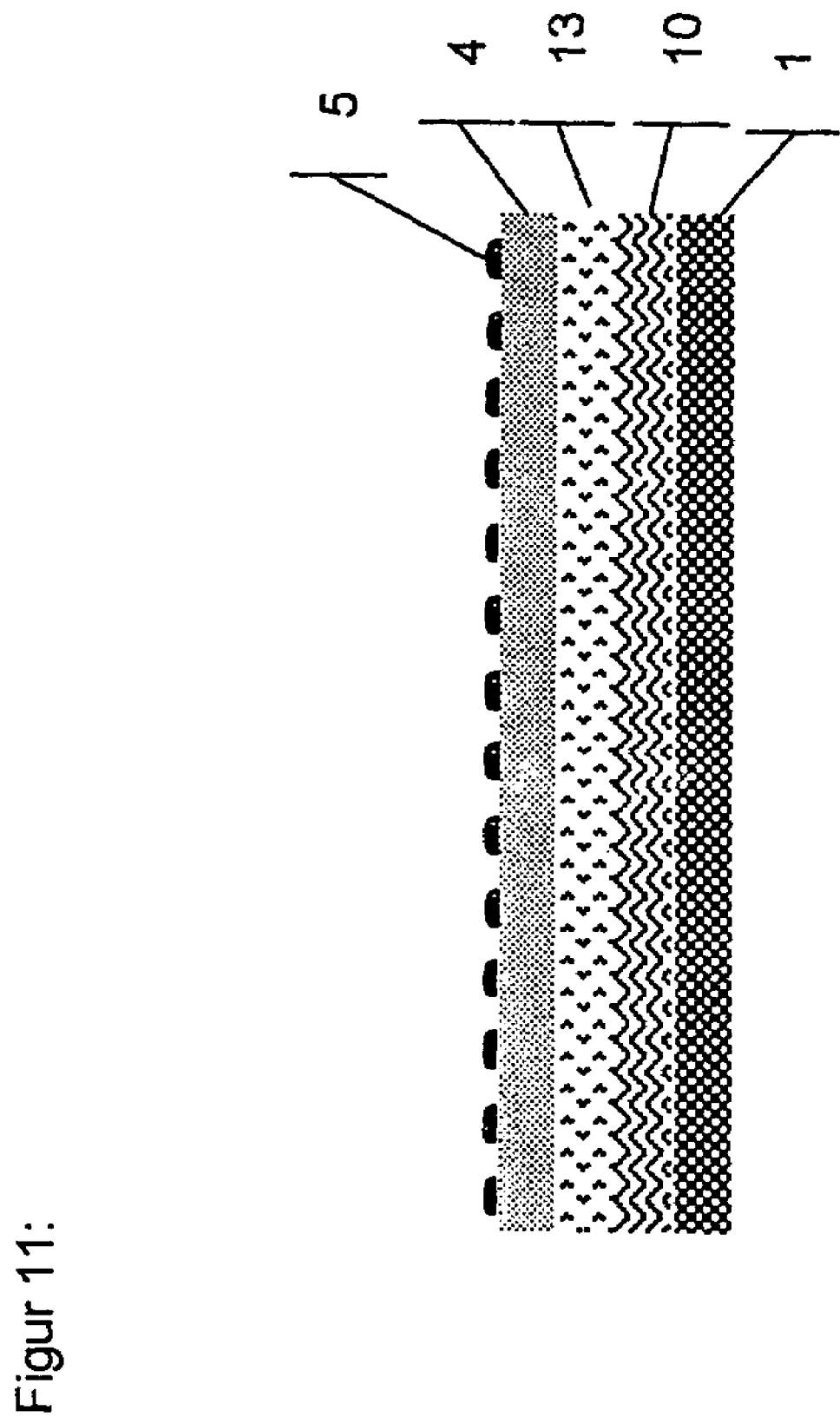
Figur 11:

ABSORBING AGENTS AND COVER LAYER WHICH IS IMPERMEABLE TO ACTIVE SUBSTANCES AND WHICH CONTAINS CHANNEL-FORMERS OR REMOVABLE PROTECTIVE LAYER OF A TRANSDERMAL THERAPEUTIC SYSTEM

This present invention concerns a cover layer that is impermeable to the active substances or a removable protective layer of a transdermal therapeutic system containing absorbing agents and channel-forming agents.

BACKGROUND AND SUMMARY OF THE INVENTION

The cover layers used in conventional transdermal therapeutic systems are films made from acetal, acrylate, acrylonitrile butadiene styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol polymer, ionomers, nylon (polyamide), nylon copolymer, polybutylene, polycarbonate, polyester, polyethylene terephthalate, thermoplastic polyester copolymer, polyethylene copolymer (high-density), polyethylene (high molecular weight, high-density), polyethylene (intermediate molecular weight, high-density), polyethylene (linear low-density), polyethylene (low density), polyethylene (medium density), polyethylene oxide, polyimide, polypropylene, polypropylene (coated), polypropylene (oriented), polystyrene, polyurethane, polyvinyl acetate, polyvinyl chloride, polyvinylidene chloride, and/or styrene acrylonitrile, which, if required, may have been metallized or pigmented. They serve to stabilize the active substance-containing system and protect it against external influences. The cover layer is impermeable to the active substances and therefore prevents the active substance from diffusing to the outside.

The removable protective layers that are used in transdermal therapeutic systems are also impermeable to the active substances and are usually made from polyester, polyethylene, polypropylene, polysiloxane, polyacrylate, ethylene vinyl acetate, polyurethane, polyisobutene or paper, in most cases coated with silicon and/or polyethylene, or a composite of these. They also serve to stabilize the active substance-containing system and protect it against external influences. The removable protective layer is impermeable to the active substances and therefore prevents the active substance from diffusing to the outside during storage.

Transdermal therapeutic systems are usually packaged in sachets. The sachets are usually made from a laminate material coated with aluminum. Such coating increases the impermeability to humidity and oxygen of the packaging. Permeability depends on the thickness of the coating. As the thickness of the aluminum coating increases, environmental incompatibility and the costs incurred in manufacturing and disposing of the packaging increases. In practice, however, total impermeability can not be attained. For that reason, the transdermal therapeutic system is always exposed to a certain degree of humidity. In addition, after production, the transdermal therapeutic system releases a certain amount of residual humidity to the environment. To ensure suitable storage stability, in the sachet, an inlay can be placed which contains a drying agent. As a result, however, the packaging of the transdermal therapeutic system becomes more complicated and significantly more expensive. Highly odorous substances such as amines and polymer monomers which are released during storage from the active substance or the pressure-sensitive adhesive layer can not be eliminated at all or only partially by using this method.

The object of this present invention is to increase the storage stability of transdermal therapeutic systems by minimizing the negative impact of humidity, oxygen, free amines and/or free polymer monomers on the stability of the transdermal therapeutic systems. At the same time, the transdermal therapeutic systems are to be manufactured by conventional means, without any complicated additional production steps, and packaging costs are to be reduced simultaneously.

Surprisingly, it has been possible to achieve the object of this present invention by using, as a cover layer that is impermeable to the active substances or as a removable protective layer of the transdermal therapeutic system, a polymer in the form of a film which either directly contains the absorbing agents and channel-forming agents or which is coated with a polymer support containing these substances. The coating can be applied either over the entire surface of the film or in patterns (e.g. in a grid pattern) directly during production.

The company Capitol Specialty Plastics holds several patent applications (WO 00/17259, WO 00/17260, WO 00/16884, WO 99/62697, WO 99/61856, WO 98/39231, WO 99/61855, WO 00/17258, WO 99/63288, U.S. Pat. No. 5,911,937) which claim polymers containing absorbing agents, releasing agents, channel-forming agents, etc. These polymers are mainly used to eliminate humidity from packages. They are either inlays that are placed in the packages, or the packages are lined therewith. The thickness of the inlays and coating films described is $\geq 400$ μm. This is disadvantageous insofar as these inlays or coatings require an additional production step and represent another cost factor.

By using the cover layer and/or removable protective layer in accordance with this present invention, the thickness of the aluminum coating of the packaging can be greatly reduced. This benefits the environment and reduces the costs of the packaging. The manufacturing process need not be changed. Common state-of-the-art manufacturing processes can continue to be used. In addition, no additional drying element needs to be placed in the packaging. The manufacturing costs of the TTS can therefore be significantly reduced.

DETAILED DESCRIPTION OF THE INVENTION

The transdermal therapeutic system (TTS) can be stored in a stable manner over long periods of time. Even under extreme conditions, such as in the tropics, the transdermal therapeutic system can be stored without additional elements for a prolonged period of time without a loss of stability. Furthermore, TTS with humidity-sensitive active substances can be stored without stability problems. In these cases, the storage time can even be extended.

The cover layer that is impermeable to the active substances or removable protective layer of a transdermal therapeutic system in accordance with this present invention is made from a polymer, (i) which either contains the absorbing agents and channel-forming agents directly, or (ii) is coated with a polymer support containing these substances. The polymer support can be applied either over the entire surface of the film or in patterns directly during production. In case a separate polymer support is used, the cover layer and/or the protective layer and the polymer support can be made from either the same or different materials.

The polymers used in the mixture of the polymer (for the polymer support or the cover layer and/or the removable protective layers) may be polyolefins, such as polyethylene and/or polypropylene, polyisoprenes, polybutadienes, polybutenes, polysiloxanes, polyamides, ethylene vinyl acetate copolymers, ethylene methacrylate copolymers, polystyrenes, polyesters, polyanhydrides, polyacrylate nitrites, polysulfonates, polyesteramides, polyacrylate esters, propylene maleic anhydride, polyethylene maleic anhydride, polyethylene urethanes, polyethylene ethyl vinyl alcohols, polyethylene nylon, and/or polyurethanes.

Furthermore, the polymer may be a crosslinkable polymer which can be crosslinked by means of heat or radiation, in particular by means of UV. Therefore, the polymer of the polymer support or of the cover layer and/or of the removable protective layer can be crosslinkable. In case a separate polymer layer is present, a thermally crosslinkable polymer can be applied cold or under heat onto the cover layer and/or protective layer; a polymer that can be crosslinked under radiation can be crosslinked cold or hot. Crosslinking may be performed after the respective application.

The polymer content is 10–90 percent by weight based on the total weight of the mixture of the polymer, channel-forming agents, and absorbing agents, regardless of whether it is used directly as a film or as a coating.

The channel-forming agents used in this present invention can be hydrophilic substances such as, for example, polyglycols, ethyl vinyl alcohols, glycerin, pentaerythritol, polyvinyl alcohols, polyvinyl pyrrolidone, vinyl pyrrolidone, N-methyl pyrrolidone, polysaccharides, saccharides, and/or sugar alcohols. As polyglycols, polyethylene glycol and/or polypropylene glycol are preferred. As saccharides, e.g. glucose, mannose, galactose, and/or fructose can be used. As sugar alcohols, mannitol, sorbitol, hexitol, dulcitol, xylitol, ribitol, and/or erythrol can be used, among others. The term "polysaccharides" may mean, for example, dextrines and/or hydrolyzed starch.

The content of the channel-forming agents can be 10–40 percent by weight, based on the total weight of the mixture of the polymer, channel-forming agents, and absorbing agents.

Different types of absorbing agents can be incorporated in the cover layer or removable protective layer.

One embodiment of this present invention contains drying agents as absorbing agents. There are three different types of drying agents.

One group contains chemical substances which form hydrates with water. Examples for such chemical substances are water-free salts which tend to absorb water or humidity while forming a stable hydrate. During this reaction, the humidity is retained, and its release as a result of a chemical reaction is prevented.

The second group of drying agents contains reactive substances. These substances react with water or humidity by forming a new substance. The newly formed substances are normally stable at low temperatures. Their formation can only be reversed by using high energy. This type of drying agents is mainly used in drying solvents and as a water-absorbing material in polymers which themselves need to remain in a humidity-reduced state.

The third group of drying agents retains humidity by means of physical absorption. The drying agent particles have a fine capillary structure, as a result of which the humidity is drawn into these capillaries. The pore size of the capillaries as well as the capillary density determine the absorption properties of the drying agent. Examples for this type of drying agents include molecular sieves, silicon gels, earths (e.g. montmorillimite earth), certain synthetic polymers (e.g. polymers used in baby diapers), and starches.

This group of drying agents is preferred due to its inertness and lack of solubility in water.

One preferred embodiment in accordance with this present invention contains, as a drying agent, molecular sieves with a pore size of 3–15 Å.

Another embodiment in accordance with this present invention contains silicon gel with a pore size of 24 Å.

As other potential absorbing agents, metals and alloys, such as, for example, nickel, copper, aluminum, silver and/or gold, metal-coated particles, such as, for example, silver-coated copper, silver-coated nickel and/or silver-coated glass microspheres, inorganic substances, such as, for example, barium titanium trioxide, strontium titanium trioxide, silicon dioxide, aluminum oxide, zinc oxide, titanium dioxide, manganese oxide, copper oxide, antimony oxide, molten silicon, amorphous molten silicon, ion-exchange resins, lithium-containing metal oxides, hollow glass microspheres, silicon sol-gel, titanium sol-gel and/or mixed titanium, carbon-based substances, such as, for example, carbon, activated charcoal and/or diamond powder, elastomers, such as, for example, polybutadiene and/or polysiloxanes, semi-metals, and/or ceramic material can be used.

The content of the absorbing agent(s) can be 10 to 70 percent by weight, based on the total weight of the mixture of the polymer, channel-forming agents, and absorbing agents.

The content must not be too high since otherwise, the cover layer becomes brittle. In case the content is too low, protection against humidity is not sufficient.

The absorbing agents incorporated in the polymer are uniformly distributed in the polymer and/or the film. The channel-forming agents incorporated in the polymer form channels which extend through the entire film and/or through the pattern that has been created from the outside towards the inside. Oxygen, humidity, or other undesired substances can therefore migrate from the outer environment into the interior of the film and/or pattern and react with the absorbing agents in the interior of the film and/or pattern. The absorption rate is many times higher since a larger number of absorbing agent particles can react with the undesired substances than in the absence of channel-forming agents. Depending on which channel-forming agents are selected, finer and therefore a larger number of channels with increased branches or larger, less branched channels in a smaller number can be created in the polymer. The finer the channels, the larger the absorption rate for undesired substances.

If desired, pharmaceutically safe coloring agents can be added to the mixture of the polymer, channel-forming agents, and absorbing agents.

In case the cover layer or removable protective layer is made from a film with integrated channel-forming agents and absorbing agents, the thickness of the layer is 5–100 µm, in particular 15–40 µm, preferably 15 µm.

In case the cover layer or removable protective layer is made from a conventional film, which, either over its entire surface or in a pattern, has been coated with a mixture of the polymer, channel-forming agents, and absorbing agents, the thickness can be adjusted to any desired value. The only factor which needs to be considered is flexibility. Flexibility must ensure satisfactory use of the transdermal therapeutic system.

In accordance with this present invention, the film that is conventionally used for a cover layer that is impermeable to the active substances (4) can be coated with the mixture (5) on the top side and/or bottom side.

In accordance with this present invention, the film that is conventionally used for the removable protective layer can be coated with the mixture on the side facing outwards.

The term "transdermal therapeutic system" refers to a band (aid). Such a band may be a matrix or membrane system comprising a cover layer that is impermeable to the active substances (4) and a removable protective layer (1). Both layers or only one of the layers can be provided with the channel-forming agents and absorbing agents.

In case a separate polymer support is provided, for the removable protective layer, polyester, polyethylene, polypropylene, polysiloxanes, polyacrylate, ethylene vinyl acetate, polyurethane, polyisobutene or paper, in most cases coated with silicon and/or polyethylene, or a composite can be used as conventional films.

In case a separate polymer support is provided, the cover layers used in conventional transdermal therapeutic systems can be used as films made from acetal, acrylate, acrylonitrile butadiene styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol polymer, ionomers, nylon (polyamide), nylon (polyamide) copolymer, polybutylene, polycarbonate, polyester, polyethylene terephthalate, thermoplastic polyester copolymer, polyethylene copolymer (high-density), polyethylene (high-molecular-weight, high-density), polyethylene (intermediate-molecular-weight, high-density), polyethylene (linear low-density), polyethylene (low density), polyethylene (medium-density), polyethylene oxide, polyimide, polypropylene, polypropylene (coated), polypropylene (oriented), polystyrene, polyurethane, polyvinyl acetate, polyvinyl chloride, polyvinylidene chloride and/or styrene acrylonitrile, which, if needed, may be metallized or pigmented.

In accordance with one embodiment, the matrix band comprises the cover layer that is impermeable to the active substances (4), one or several self-adhesive matrix layer(s) (2) containing the active substance and/or permeation-enhancing agents or one or several matrix layer(s) (13) coated with a pressure-sensitive adhesive (10), and a removable protective layer (1).

For the matrix, the matrix-forming agents commonly used in medicine such as polyacrylate, silicon, polyisobutylene, rubber, rubber-like synthetic homopolymers, copolymers or block polymers, butyl rubber, styrene/isoprene copolymerizate, polyurethanes, copolymers of ethylene, polysiloxanes, styrene/butadiene copolymerizate or a mixture thereof in accordance with the state of the art are used.

As an adhesive, polydimethyl siloxane, polyacrylates, polyisobutylene, polyacrylate with $C_4$–$C_{10}$ alkyl alcohol esters, polyurethane, polyvinyl ether, amine-resistant silicon in ethyl acetate or n-heptane, polyisobutylene/mineral oil, or a mixture thereof can be used.

Another embodiment in accordance with this present invention represents a membrane system. Such system comprises the cover layer that is impermeable to the active substances (4), an active substance-containing reservoir or a reservoir layer (12), a semipermeable membrane (11), an optional pressure-sensitive adhesive (10), and a removable protective layer (1).

The reservoir contains the active substance(s) and/or permeation-enhancing agents, stabilizing agents, emulsifiers, thickening agents, and/or common adjuvants for membrane systems and/or reservoir bands. The reservoir and/or the reservoir layer is located between the cover layer and the membrane. As gelling agents, if needed, methyl cellulose, hydroxypropyl cellulose, hydroxyl ethyl cellulose, carboxyvinyl polymer, sodium ply oxilate, carboxymethylcellulose, or a mixture thereof can be used.

The membrane, which usually consists of inert polymers, in particular on the basis of polypropylene, polyvinyl acetate, polyamide, ethylene vinyl acetate copolymers and/or silicon, can have an effect controlling the release of the active substance, depending on pore size.

For the pressure-sensitive adhesive layer, a pressure-sensitive adhesive, for example on the basis of polyurethane, polyisobutylene, polyvinyl ether, silicon, polyacrylate, or a mixture thereof can be chosen.

The silicon-based adhesive may be a silicon adhesive based on two main components: a polymer or adhesive, in particular polysiloxane, and an adhesiveness-increasing resin. The polysiloxane adhesive is usually prepared with a cross-linking agent for the adhesive, typically with a highly molecular polydiorganosiloxane, as well as with the resin to produce, by means of a suitable organic solvent, a three-dimensional silicate structure. Admixing the resin to the polymer is the most important factor to modify the physical properties of the polysiloxane adhesive; compare, for example, Sobieski, et al., "Silicone Pressure Sensitive Adhesives", Handbook of Pressure Sensitive Adhesive Technology, $2^{nd}$ ed., pp. 508–517 (D. Satas, ed.), Van Nostrand Reinhold, New [Adhe]sive Technology, $2^{nd}$ ed., pp. 508–517 (D. Satas, ed.), Van Nostrand Reinhold, New York (1989).

Another example for a pressure-sensitive adhesive on a silicon basis is trimethylated silicon dioxide that has been treated with polydimethyl siloxane with trimethylsiloxy groups in the end position.

The adhesives on a polyacrylate basis can be any desired homopolymer, copolymer, or terpolymer consisting of different acrylic acid derivatives.

The polyacrylates may be polymers of one or several monomers of acrylic acids and other copolymerizable monomers. In addition, the acrylate polymers can comprise copolymers of alkyl acrylates and/or methacrylates and/or copolymerizable secondary monomers or monomers with functional groups. Once the quantity of each type that is added as a monomer is changed, the cohesive properties of the resulting acrylate polymers can be modified. In general, the acrylate polymer consists of at least 50 percent by weight of an acrylate, methacrylate, alkyl acrylate or alkyl methacrylate monomer, 0 to 20% of a functional monomer, copolymerizable with acrylate, and 0 to 50% of another monomer.

The following is a list of different acrylate monomers, such as, for example, acrylic acid, methacrylic acid, butyl acrylate, butyl methacrylate, hexyl acrylate, hexyl methacrylate, isooctyl acrylate, isooctyl methacrylate, glycidyl methacrylate, 2-hydroxyethyl acrylate, methyl acrylate, methyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate, which can be polymerized alone or as a mixture.

In addition, functional monomers that are copolymerizable with the above acrylates, such as, for example, acrylic acid, methacrylic acid, maleic acid, maleic anhydride, hydroxyethyl acrylate, hydroxypropyl acrylate, acrylamide, dimethylacrylamide, acrylnitrile, dimethylaminoethyl acrylate, dimethylaminoethyl methacrylate, tert. butylaminoethyl acrylate, ter. butylaminoethyl methacrylate, methoxy ethyl acrylate, vinyl acetate, and methoxy ethyl methacrylate can be used in the copolymerization.

Further details and examples for pressure-sensitive acrylates that are suitable for this present invention are described in Satas Handbook of Pressure Sensitive Adhesive Technology "Acrylic Adhesives", 2$^{nd}$ ed., pp. 396–456 (D. Satas, ed.), Van Nostrand Reinhold, New York (1989).

The active substance contained in the transdermal therapeutic system may, for example, be a member of the group of active substances such as corticoids, androgens, estrogens, gestagens, proton pump inhibitors, 5-HT$_1$ antagonists, sympatholytic agents/sympathomimetic agents, anticholinergic agents, tranquilizers/anxiolytic agents, cessation agents, analgesics, calcium antagonists, antiemetics, vasodilators, opiate antagonists, coagulation inhibitors, Antiparkinson agents, antidementia agents/cholinesterase inhibitors, ACE inhibitors, antihistamine agents, ulcer therapy agents/H$_2$ receptor blockers, angiotensin II antagonists, neuroleptics, antidepressants, local anesthetics, and/or lipid reducers.

The transdermal therapeutic system may contain one or several members of the group of corticoids, such as beclomethasone, budesonide propionate, flunisolide acetate, triamcinolone, fluticasone, betamethasone-17-valerate, glycine acid, fluocortolone, beclomethasone dipropionate, budesonide base, dexamethasone, hydrocortisone, flunisolide, prednisone, triamcinolone acetonide, methylprednisolone, betamethasone, deflazacort, cortisone, cortisone acetate, prednylidene, cloprednol, fluocortolone-21-hexanoate, prednicarbate, and/or their derivatives and/or their pharmaceutically safe salts, as a component of the active substance.

The transdermal therapeutic system may contain one or several members of the group of androgens, such as testosterone, testosterone undecanoate, androsterone, and/or their derivatives and/or their pharmaceutically safe salts, as a component of the active substance.

The transdermal therapeutic system may contain one or several members of the group of estrogens, such as estradiol, estradiol benzoate, estradiol valerate, estradiol dipropionate, estron, estriol, ethinyl estradiol, diethylstilbestrol, diethylstilbestrol dimethylether, diethylstilbestrol diphosphate, diethylstilbestrol dipropionate, and/or their derivatives and/or their other pharmaceutically safe salts, as a component of the active substance.

The transdermal therapeutic system may contain one or several members of the group of gestagens, such as progesterone, cyproterone acetate, cyproterone, chlormadinone, chlormadinone acetate, medroxyprogesterone acetate, levonorgestrel, norgestrel, norgestimate, norethisterone acetate, and/or their derivatives and/or their other pharmaceutically safe salts, as a component of the active substance.

The transdermal therapeutic system may contain one or several members of the group of proton-pump inhibitors, such as omeprazole, esomeprazole, lansoprazol, leminoprazole, pantoprazole, rabeprazole, polaprezinc, and/or their derivatives and/or their pharmaceutically safe salts, as a component of the active substance.

The transdermal therapeutic system may contain one or several members of the group of antimigraine agents and/or 5-HT$_1$ antagonists, such as lisuride, sumatriptan, sumatriptan hydrogen succinate, rizatriptan, rizatriptan benzoate, almotriptan, avitriptan, eletriptan, frovatriptan, naratriptan, zolmitriptan, and/or their derivatives, and/or their other pharmaceutically safe salts, as a component of the active substance.

The transdermal therapeutic system may contain one or several members of the group of sympatholytic agents/sympathomimetic agents, such as adimolol, adrenalin, albuterol, alprenolol, amosulalol, arotinolol, atenolol, bambuterol, betaxolol, bevantolol, bisoprolol, bitolterol, bopindolol, broxaterol, bucindolol, bucumolol, bufuralol, bunitrolol, bupranolol, butofilolol, carazolol, carbuterol, carteolol, carvedilol, cetamolol, cicloprolol, clenbuterol, cloranolol, carteolol, dihydroergotamine, dihydroergotamine tartrate, dihydroergotamine mesylate, dilevalol, doxazosin, etilefrine, epanolol, esatenolol, esmolol, fenetylline, fenoterol, formoterol, ibuterol, isoprenaline, labetalol, landiolol, levobetaxolol, levobunolol, levosalbutamol, mabuterol, mepindolol, metipranolol, metoprolol, morazone, nebivolol, nipradilol, norfenefrine, noradrenalin, oxprenolol, penbutolol, picumeterol, pimolol, pindolol, pirbuterol, phenmetrazine, phenylephrine, phentolamine, phenoxybenzamine, prazosine, procaterol, propanolol, rimiterol, reproterol, salbutamol, salmeterol, sotalol, sulfonterol, terazosin, terbutaline, tertatolol, tienoxolol, tilisolol, timolol, tolazoline, toliprolol, tolubuterol, tamsulosine, clonidine, moxonidine, and/or their derivatives and/or their pharmaceutically safe salts, as a component of the active substance.

The transdermal therapeutic system may contain one or several members of the group of anticholinergic agents, such as ipratropium, oxitropium, atropine, scopolamine base, ipratropium bromide, oxitropium bromide, atropine methyl bromide, atropine methyl nitrate, atropine sulfate, atropine valerianate, scopolamine hydrobromide, scopolamine hydrochloride, scopolamine hydroiodide, tropicamide, oxybutinine, and/or their derivatives and/or their other pharmaceutically safe salts, as a component of the active substance.

The transdermal therapeutic system may contain one or several members of the group of tranquilizers/anxiolytic agents, such as alprazolam, bentazepam, bromazepam, camazepam, clorazepate, clonazepam, clotiazepam, diazepam, etiracetam, etizolam, fludiazepam, flunitrazepam, flurazepam, flutazolam, flutoprazepam, halazepami ketazolam, loprazolam, lorazepam, lormetazepam, medazepam, metaclazapam, mexazolam, midazolam, nitrazepam, norazepam, oxazepam, oxazolam, prazepam, temazepam, triazolam, and/or their derivatives and/or their pharmaceutically safe salts, as a component of the active substance.

The transdermal therapeutic system may contain one or several members of the group of cessation agents, such as nicotine, methadone, disulfirame, lobeline, and/or their derivatives and/or their pharmaceutically safe salts, as a component of the active substance.

The transdermal therapeutic system may contain one or several members of the group of analgesics, such as ibuprofen, ketoprofen, alminoprofen, bermoprofen, carprofen, dexibuprofen, dexketoprofen, fenoprofen, flobufen, flunoxaprofen, flurbiprofen, loxoprofen, pelobiprofen, pranoprofen, pentazocine, tilnoprofen, ximoprofen, zaltroprofen, diclofenac, amfenac, bromfenac, clidanac, etodolac, felbinac, fentiazac, mofezolac, oxindanac, tifurac, indomethacin, acemetacin, piroxicam, ampiroxicam, meloxicam, isoxicam, lornoxicam, tenoxicam, butorphanol buprenorphine, morphine, hydromorphone, dihydrocodeine, oxycodone, piritramide, pentazocine, levomethadone, tramadol, fentanyl, codeine, codeine hydrochloride, codeine phosphate, tilidine, tilidine mesylate, tilidine hydrochloride, diclofenac sodium, amfenac sodium, bromfenac sodium, clidanac sodium, etodolac sodium, felbinac sodium, fentiazac sodium, mofezolac sodium, oxindanac sodium, tifurac sodium, indomethacin sodium, acemetacin sodium, meloxicam cyclodextrin, buprenorphine hydrochloride, morphine acetate, hydromorphone hydrochloride, oxycodone hydrochloride, piritramide hydrogen tartrate, levomethadone hydrochloride, fentanyl dihydrogen citrate, and/or their derivatives and/or their other pharmaceutically safe salts, as a component of the active substance.

The transdermal therapeutic system may contain one or several members of the group of calcium antagonists, such as amlodipine, arandipine, azelmidipine, barnidipine, benidipine, cilnidipine, efonidipine, felodipine, flordipine, iganidipine, isradipine, lacidipine, lercanidipine, manidipine, nicardipine, nifedipine, nilvadipine, nisoldipine, nitrendipine, palonidipine, pranidipine, ticlopidine, vatanidipine, clentiazem, and/or their derivatives and/or their pharmaceutically safe salts, as a component of the active substance.

The transdermal therapeutic system may contain one or several members of the group of antiemetics, such as alizapride, azasetron, batanopride, clebopride, dazopride, dolasetron, domperidone, granisetron, itasetron, levosulpiride, metoclopramide, nabilone, ondansetron, pancopride, ramosetron, tropisetron, zatosetron, and/or their derivatives and/or their pharmaceutically safe salts, as a component of the active substance.

The transdermal therapeutic system may contain one or several members of the group of vasodilators, such as glycerol trinitrate (nitroglycerin), isosorbide dinitrate, isosorbide-5-mononitrate, pentaerythrityl tetranitrate, molsidomine, and/or their derivatives and/or their other pharmaceutically safe salts, as a component of the active substance.

The transdermal therapeutic system may contain one or several members of the group of opiate antagonists, such as naloxone, naltrexone, and/or their derivatives and/or their pharmaceutically safe salts, as a component of the active substance.

The transdermal therapeutic system may contain one or several members of the group of coagulation inhibitors, such as heparin sodium, certoparin, dalteparin, danaparoid, enoxaparin, nadroparin, reviparin, tinzaparin, heparinoid, warfarin, phenprocoumon, acenocoumarol, and/or their derivatives and/or their pharmaceutically safe salts, as a component of the active substance.

The transdermal therapeutic system may contain one or several members of the group of Antiparkinson agents, such as aptiganel, biperiden, budipine, cabergoline, droxidopa, entacapone, idazoxan, lazabemide, milacemide, mofegiline, pergolide (pergolide mesylate, pergolide hydrochloride), pramipexole, quinelorane, rasagiline, remacemide, ropinorole, selegiline, talipexole, tolcapone, and/or their derivatives and/or their other pharmaceutically safe salts, as a component of the active substance.

The transdermal therapeutic system may contain one or several members of the group of antidementia agents/cholinesterase inhibitors e.g. rivastigmine, neostigmine, physostigmine, pyridostigmine, donepezil, tacrine, and/or their derivatives and/or their other pharmaceutically safe salts, as a component of the active substance.

The transdermal therapeutic system may contain one or several members of the group of ACE inhibitors, such as alacepril, benazepril, captopril, ceronapril, cilazapril, denapril, enalapril, enalapril maleate, fosinopril, imidapril, lisinopril, moexipril, moveltipril, perindopril, quinapril, ramipril, ramiprilat, ramipril mesylate, rentiapril, spirapril, temocapril, trandolapril, trandolapril mesylate, utibapril, zofenopril, and/or their derivatives and/or their other pharmaceutically safe salts, as a component of the active substance.

The transdermal therapeutic system may contain one or several members of the group of antihistamine agents, such as acrivastine, astemizole, carebastine, cetirizine, descarbethoxy loratadine, dimethindene, ebastine, emedastine, epinastine, fexofenadine, ketotifen, levocabastine, loratadine, mequitazine, mizolastine, nafamostat, norastemizole, olopatidine, oxatomide, rupatadine, tazifylline, temelastine, traxanox, and/or their derivatives and/or their other pharmaceutically safe salts, as a component of the active substance.

The transdermal therapeutic system may contain one or several members of the group of ulcer therapy agents/H2 receptor blockers, such as dalcotidine, famotidine, lafutidine, niperdidine, nizatidine, osutidine, pibutidine, pirenzepine, ramixotidine, ranitidine, proglumide, misoprostol, and/or their derivatives and/or their pharmaceutically safe salts, as a component of the active substance.

The transdermal therapeutic system may contain one or several members of the group of angiotensin II antagonists, such as candesartan, candesartan cilexetil, losartan, tasosartan, telmisartan, and/or their derivatives and/or their pharmaceutically safe salts, as a component of the active substance.

The transdermal therapeutic system may contain one or several members of the group of neuroleptics, such as sulpiride, promethazine, benperidol, haloperidol, chlorprothixene, clozapine, fluphenazine, perphenazine, droperidol, pipamperone, prothipendyl, melperone, flupenthixol decanoate, fluspirelene, bromperidol, levomepromazine hydrogen maleate, zotepine, pimozide, perazine, chlorpromethazine, triflupromethazine, risperidone, sertindole, amisulpride, olanzapine, zuclopenthixol, thioridazine, and/or their derivatives and/or their pharmaceutically safe salts, as a component of the active substance.

The transdermal therapeutic system may contain one or several members of the group of antidepressants, such as amitriptyline, clomipramine, maprotiline, doxepin, citalopram, fluvoxamine, reboxetine, alprazolam, fluoxetine, lofepramine, mianserin, and/or their derivatives and/or their pharmaceutically safe salts, as a component of the active substance.

The transdermal therapeutic system may contain one or several members of the group of local anesthetics, such as lidocaine, prilocaine, benzocaine, cocaine, procaine, tetracaine, bupivacaine, cinchocaine, etidocaine, mepivacaine, butanilicaine, levobupivacaine, ropivacaine, and/or their derivatives and/or their pharmaceutically safe salts, as a component of the active substance.

The transdermal therapeutic system may contain one or several members of the group of lipid reducers, such as colestyramine, xantinol nicotinate, fluvastatin, simvastatin, atorvastatin, pravastatin, cerivastatin, dalvastatin, itavastatin, lovastatin, dextrothyroxine sodium, and/or their derivatives and/or their pharmaceutically safe salts, as a component of the active substance.

The active substance contained in the transdermal therapeutic system, however, may also be leflunomide, indapamide, hydroxytamoxifen, fusidine acid, finasteride, tirofiban, rosiglitazone, pioglitazone, montelukast, and/or their derivatives and/or their pharmaceutically safe salts.

The term "pharmaceutically safe salts" of the above active substances refers to acid addition salts. They are obtained through the reaction of the active substance in the free form with pharmaceutically safe acids. Pharmaceutically safe acids are inorganic acids (e.g. muriatic acid, hydrobromic acid, sulfuric acid, nitric acid, phosphoric acid) or organic acids (e.g. acetic, propionic, hydroxy acetic, lactic, pyruvic, oxalic, maleic, malonic, succinic, fumaric, malic, tartaric, citric, methane sulfonic, ethane sulfonic, benzene sulfonic, p-toluene sulfonic, cyclohexane sulfamine, salicylic, p-amino salicylic and pamoic acid). The term "acid addition salts" also refers to solvates containing the active substance. Such solvates include, for example, hydrates, alcoholates, and the like.

In terms of other potential, pharmaceutically safe salts of the above active substances, mainly alkali metal and/or earth alkali metal salts as well as the ammonium salt may be suited, such as, for example, the potassium, sodium, lithium, calcium, magnesium, and ammonium salt.

As permeation-enhancing agents, optionally monovalent and/or plurivalent aliphatic, cycloaliphatic and/or aromatic-aliphatic alcohols with up to eight C atoms each, e.g. ethanol, 1,2-propanediol, dexpanthenol and/or polyethylene glycol; alcohol/water-mixtures; saturated and/or unsaturated fatty alcohols with 8–18 C atoms each; terpenes; e.g. cineol, carveol, menthone, terpineol, verbenone, menthol, limonene, thymol, cymene, terpinene-4-ol, neomenthol, geraniol, fenchone; mixtures of terpenes and ethanol and/or propylene glycol; tea tree oil; saturated and/or unsaturated cyclic ketones; alkyl methyl sulfoxides; saturated and/or unsaturated fatty acids with 8–18 C atoms each; their esters and salts; natural vitamin E; synthetic vitamin E and/or vitamin E derivatives; sorbitan fatty acid esters and ethoxylated sorbitan fatty acid esters; azones (laurocapram); azones mixed with alcohols; carbamide; 1-alkyl pyrrolidone; block copolymers of polyethylene glycol and dimethyl siloxanes with a cationic group at the end; isopropyl myristate, isopropyl palmitate, folate polyethylene glycol liposome, proliposome; polyoxyethylene-10-stearyl ether; a mixture of polyoxyethylene-10-stearyl ether and glyceryl dilaurate; dodecyl-2-(N,N-dimethylamino)-propanol tetradecanoate and/or dodecyl-2-(N,N-dimethylamino)-propianate; N-acetyl prolinate esters with >8 C atoms; non-ionic surfactants, e.g. lauryl ether, esters of polyoxyethylene; ethosome (phospholipids vesicle) dimethyl(arylimino)sulfurane; mixture from oil acid analogs and propylene glycol; mixture of Padimate O, octyl salicylate, octyl methoxycinnamate, laurocapram; highly dispersive silicon dioxide (Aerosil®); polyoxyethylene 7-glycerol monococoate (Cetiol® HE); 2-octyl dodecanol (Eutanol® G), or a mixture of individual components can be used.

BRIEF DESCRIPTION OF THE DRAWINGS

FIG. 1 shows the lamination of the cover layer (3). comprising a polymer, channel-forming agents, and absorbing agents onto the laminate containing the self-adhesive matrix (2) and the removable protective layer (1). The laminate pulled off a reel (6) and applied onto the laminate by means of the laminating roller (7).

FIG. 2 shows the application of the mixture (5) comprising a polymer, channel-forming agents, and absorbing agents, with a roller application system (8) onto the top side of the cover layer (4) as well as subsequent lamination with the laminating roller (7) of the cover layer (4), which has now been partially coated with the mixture (5), onto the laminate containing the self-adhesive matrix (2) and the removable protective layer (1).

FIG. 3 shows the application of the mixture (5) comprising a polymer, channel-forming agents, and absorbing agents, with a roller application system (8) onto the top side of the cover layer (4), which is a component of the laminate, which additionally contains the self-adhesive matrix (2) and the removable protective layer (1). Once the mixture has been applied, the band (9) is punched out, and the waste is removed.

FIG. 4 shows the application of the mixture (5) comprising a poclyer, channel-forming agents, and absorbing agents, with a roller application system (8) onto the bottom side of the cover layer (4) as well as subsequent lamination with the laminating roller (7) of the cover layer (4), which has now been partially coated with the mixture (5), onto the laminate containing the self-adhesive matrix (2) and the removable protective layer (1).

FIG. 5 shows the application of the mixture (5) comprising a polymer, channel-forming agents, and absorbing agents, with a roller application system (8) onto the outward-facing side of the removable protective layer (1), which is a component of the laminate, which additionally contains the self-adhesive matrix (2) and the cover layer (4). Once the mixture has been applied, the band (9) is punched out, and the waste is removed.

FIG. 6 is a top view onto the laminate, consisting of the cover layer (3), containing at least one polymer, channel-forming agents, and absorbing agents, the self-adhesive matrix (2) and the removable protective layer (1) and depicts the different production steps to obtain a packaged transdermal therapeutic system. In step A, the contours of the transdermal therapeutic system are punched out of the laminate. Step B shows the removal of the waste. In step C, the external contours of the transdermal therapeutic system are punched out. Step D shows the transdermal therapeutic system after the waste removal step. E shows the transdermal therapeutic system with a punched-on removal aid in the package sachet (transparent view).

FIG. 7 shows a cross-section of the cover layer (3) and/or removable protective layer (1) of a transdermal therapeutic system in accordance with this present invention. This cover layer (3) and/or removable protective layer (1) is formed by a polymer (16) in which the incorporated channel-forming agents form a plurality of branched channels (14). In addition, absorbing agent particles (15) are uniformly distributed in the polymer.

FIG. 8 shows a cross-section through a membrane system, consisting of the cover layer that is impermeable to the active substances (4), partially coated with the mixture of the polymer, channel-forming agents, and absorbing agents (5), a reservoir or a reservoir layer (12) containing the active substances, a membrane (11) which is permeable to the active substances, a pressure-sensitive adhesive (10), and a state-of-the-art removable protective layer (1).

FIG. 9 depicts a cross-section through a membrane system, consisting of the cover layer that is impermeable to the active substances (3) containing the channel-forming agents and absorbing agents, the conventional cover layer (4), a reservoir or a reservoir layer (12) containing the active substances, a membrane (11) which is permeable to the active substances, a pressure-sensitive adhesive (10), and a state-of-the-art removable protective layer (1).

FIG. 10 shows a cross-section through a matrix system, consisting of the cover layer that is impermeable to the active substances (3) containing the channel-forming agents and absorbing agents, a matrix layer (13) containing the active substances and optionally permeation-enhancing agents, a pressure-sensitive adhesive (10), and a state-of-the-art removable protective layer (1).

FIG. 11 shows a cross-section through a matrix system, consisting of the cover layer that is impermeable to the active substances (4), which has been partially coated with the mixture of polymer, channel-forming agents, and absorbing agents (5), a matrix layer (13) containing the active substances and optionally permeation-enhancing agents, a pressure-sensitive adhesive (10), and a state-of-the-art removable protective layer (1).

EXAMPLES

This present invention shall additionally be explained in more detail in the following examples, which are not intended to limit its scope in any manner whatsoever.

Example 1

Manufacture of a cover layer that is impermeable to the active substances or removable protective layer of a transdermal therapeutic system in accordance with this present invention in the form of a film:

First, the components polymer, channel-forming agents, and absorbing agents are mixed at an elevated temperature, and preferably, the polymer and the channel-forming agents are premixed.

The mixture is heated to the melting point and processed to form a film by using common (state-of-the-art) methods of the casting or blow-extrusion procedures. During processing, it may be necessary to partially or completely condition the ambient atmosphere in the production area (primarily reduced air humidity, reduced $O_2$ content), for example by using dried protective gases. After such production step, optionally, additional stretching of the films can be performed to modify their mechanical properties and to reduce their thickness. This production step is described in state-of-the-art literature.

The film obtained in such a manner can be stored in a suitable manner. It is used to cover a pressure-sensitive active substance-containing layer one side of which, in turn, has already been covered with a separation-coated support material and/or a support material provided with a separation coating. Optionally, this support material may initially be provided with separation-coated support materials on both sides, in which case one carrier layer must be removed immediately prior to the installation of the above film (relamination). Furthermore, the intermediate layer may consist of several sublayers, and at least one of these sublayers contains active substances. In this manner, a laminate of a separation-coated film, an active substance-containing layer or layers and a drying agent-containing layer is obtained. From this laminate, single units are obtained by punching, cutting or by using another suitable method, and such units are temporarily stored under suitable conditions or directly packaged. Again, during processing or temporary storage, it may be necessary to partially or entirely condition the ambient atmosphere in the production area (primarily reduced air humidity, reduced $O_2$ content), for example by using dried protective gases.

Example 2

Manufacture of a cover layer that is impermeable to the active substances or removable protective layer of a transdermal therapeutic system, wherein such layers have been coated with a polymer support containing absorbing agents and channel-forming agents:

First, the components polymer, channel-forming agents, and absorbing agents are mixed at an elevated temperature, and preferably, the polymer and the channel-forming agents are premixed.

Portions of the resulting mixture are packaged for subsequent processing or processed directly. For that purpose, the mixture is applied in a molten state, e.g. in an extruder or by using other suitable mixing and/or dosing devices, the basic variations of which, for example, are already commonly used in the application of hot melt adhesives. Afterwards, the mixture is applied, for example by means of nozzles or rollers, onto the film which already forms or will form a part of the active substance-containing composite, in a defined quantity and/or position. Preferably, a suitable quantity thereof will be applied onto the cover layer that is impermeable to the active substances of an active substance-containing composite immediately prior to manufacturing and packaging the individual units. Again, during processing or temporary storage, it may be necessary to partially or entirely condition the ambient atmosphere in the production area (primarily reduced air humidity, reduced $O_2$ content), for example by using dried protective gases.

Example 3

Composition of the Mixture:

| | |
|---|---|
| Polypropylene | 70 percent by weight |
| Polyethylene Glycol | 10 percent by weight |
| Molecular Sieve 4 Å | 20 percent by weight |

Example 4

Composition of the Mixture:

| | |
|---|---|
| Polypropylene | 35 percent by weight |
| Polyethylene Glycol | 12 percent by weight |
| Molecular Sieve 4 Å (Baylith ® T Powder) | 53 percent by weight |

Example 5

Composition of the Mixture:

| | |
|---|---|
| Polyethylene | 55 percent by weight |
| Polyethylene Glycol | 10 percent by weight |
| Molecular Sieve 4 Å | 20 percent by weight |

The invention claimed is:

1. A transdermal therapeutic system, wherein such system is a membrane system with
    an impermeable cover layer,
    an active substance-containing reservoir or an active substance-containing reservoir layer, and
    a microporous or semipermeable membrane,
    an optional pressure-sensitive adhesive layer, and
    a removable protective layer, wherein the cover layer or the protective layer or both are made from at least one polymer and an embedded absorbing agent and channel-forming agent or wherein the cover layer or the protective layer or both are a film that has been coated with a mixture (polymer support) of at least one polymer, channel-forming agents, and absorbing agent over its entire surface or in patterns.

2. A method for the manufacture of a transdermal therapeutic system with a layer that is impermeable to the active substances and a removable protective layer, wherein a polymer support containing the absorbing agent and the channel-forming agent is applied, either over the entire surface or in patterns, to the layer that is impermeable to the active substances and/or the removable protective layer, and wherein the transdermal therapeutic system is a matrix system with a cover layer that is impermeable to the active substances, one or several active substance-containing self-adhesive matrix layer(s) or one or several active substance-containing matrix layer(s) that have been coated with a pressure-sensitive adhesive, and a removable protective layer, wherein the cover layer or the protective layer or both are made from at least one polymer and an embedded absorbing agent and channel-forming agent or wherein the cover layer or the protective layer or both are a film that has been coated with a mixture (polymer support) of at least one polymer, at least one channel-forming agent, and at least one absorbing agent over its entire surface or in patterns; and wherein the cover layer, the protective layer or both layers have a polymer content of 10 to 90 percent by weight, based on the total weight of the mixture of the polymer, channel-forming agents, and absorbing agents; and wherein the channel forming agents are hydrophilic substances wherein the content of the channel forming agent is 10 to 40 percent by weight based on the total weight of the mixture of the polymer, channel-forming agents, and absorbing agents; and wherein the absorbing agent is selected from the group consisting of drying agents, metals, alloys, metal-coated particles, inorganic substances, ion-exchange resins, substances on the basis of carbon, in particular on the basis of elemental carbon, elastomers, semi-metals, ceramic material and mixtures thereof; and wherein the content of the absorbing agent is from 10 to 70 percent by weight based on the total weight of the mixture of the polymer, channel-forming agents, and absorbing agents; and the transdermal therapeutic system has one or several self-adhesive matrix layers.

3. The transdermal therapeutic system in accordance with claim 1, wherein the cover layer or the protective layer or both have been coated with a mixture (polymer support) consisting of at least one thermoplast, at least one channel-forming agent, and at least one absorbing agent.

4. The transdermal therapeutic system in accordance with claim 1, wherein the cover layer or the protective layer or both have been coated, whether in a cold or hot state, with a mixture (polymer support) consisting of
  (i) at least one thermally crosslinkable polymer, at least one channel-forming agent, and at least one absorbing agent, or
  (ii) at least one polymer which can be crosslinked by means of radiation, at least one channel-forming agent, and at least one absorbing agent, and in either case, the crosslinking has been performed thereinafter.

5. The transdermal therapeutic system in accordance with claim 1, wherein the film used for the cover layer that is impermeable to the active substances is coated with the mixture on its top side or bottom side or on both sides.

6. The transdermal therapeutic system in accordance with claim 1, wherein the film that is used for the removable protective layer is coated with the mixture on its outward-facing side.

7. The method in accordance with claim 2, wherein a transdermal therapeutic system with one or several matrix layers is produced which are coated with a pressure-sensitive adhesive.

8. The transdermal therapeutic system in accordance with claim 4, wherein the radiation is UV radiation.

* * * * *